United States Patent [19]

Datema et al.

[11] Patent Number: 5,409,906
[45] Date of Patent: Apr. 25, 1995

[54] α NUCLEOSIDE COMPOUNDS AND A METHOD FOR TREATING HBV USING SAID COMPOUNDS

[75] Inventors: Roelf Datema, Cheshire, Conn.; Zsuzanna M. I. Kovacs, Pietra Ligure, Italy; Karl N. G. Johansson, Enhorna, Sweden; Björn Lindborg, Älvsjö, Sweden; Goran B. Stening, Sodertalje, Sweden; Bo. F. Oberg, Uppsala, Sweden

[73] Assignee: Medivir AB, Huddinge, Sweden

[21] Appl. No.: 41,165

[22] Filed: Apr. 1, 1993

Related U.S. Application Data

[63] Continuation of Ser. No. 794,704, Nov. 20, 1991, Pat. No. 5,215,970, which is a continuation of Ser. No. 548,708, Jul. 6, 1990, abandoned, which is a continuation-in-part of Ser. No. 285,965, Dec. 12, 1988, abandoned.

[30] Foreign Application Priority Data

Apr. 16, 1987 [SE] Sweden ................................. 8701605

[51] Int. Cl.$^6$ ............................................. A61K 31/505
[52] U.S. Cl. ........................................ 514/49; 514/50; 514/885
[58] Field of Search ............................ 514/49, 50, 885

[56] References Cited

U.S. PATENT DOCUMENTS

| | | | |
|---|---|---|---|
| 3,775,397 | 11/1973 | Etzold et al. | 536/23 |
| 3,817,982 | 6/1974 | Verheyden et al. | 536/23 |
| 4,177,348 | 12/1979 | Shealy et al. | |
| 4,754,026 | 6/1988 | Kawada et al. | 536/23 |
| 4,863,906 | 9/1989 | Rahim et al. | 536/23 |

FOREIGN PATENT DOCUMENTS

| | | | |
|---|---|---|---|
| 3722 | 8/1983 | Denmark . | |
| 4066 | 8/1989 | Denmark . | |
| 0104066 | 9/1983 | European Pat. Off. . | |
| 0199451 | 3/1986 | European Pat. Off. | 536/23 |
| 356166 | 2/1990 | European Pat. Off. . | |
| 5227782 | 3/1977 | Japan | 536/23 |
| 57-146798 | 9/1982 | Japan . | |
| WO00759 | 3/1984 | WIPO . | |

OTHER PUBLICATIONS

Kilikawski et al., J. of Med. Chem., vol. 17, No. 3, pp. 269-273, (1974).
Barr et al., Chem. Soc. of London, Journal Perkin Trans I, pp. 1263-1267, (1978).
Yamaguchi et al., Chem Pharm. Bull., vol. 34, pp. 1441-1450, (1984).
Y-L Fu & M. Bobek, Nucleic Acids Chemistry, pp. 317-323 (1978).
E. J. Reist et al, J. Am. Chem. Soc., vol. 86, pp. 5658-5663 (1976).
Y. L. Fu & M. Bobek, J. Org. Chem., vol. 41,, No. 24, pp. 3831-3834 (1976).
U. G. Nayak & R. L. Whistler, Liebigs Ann. Chem., 741, pp. 131-138 (1970).
M. Bobek et al, J. Med. Chem., 18 pp. 784-787 (1975).
R. L. Whistler et al, J. Org. Chem. 36 pp. 108-110 (1971).
N. Otatani & R. L. Whistler, J. Med. Chem., 17, No. 5 pp. 535-538 (1974).
N. Otatani & R. L. Whistler, J. Med. Chem., 17, No. 5, pp. 535-537 (1974).
Y. Fulmer Shealy et al, J. Med. Chem., vol. 29, pp. 1720-1725 (1986).
Y. Fulmer Shealy et al, J. Heterocyclic Chem., vol. 20, No. 3, pp. 655-661 (1983).
Y. Fulmer Shealy et al, J. Med. Chem., vol. 26, pp. 156-161 (1983).
Y. Fulmer Shealy et al, J. Heterocyclic Chem., vol. 18, pp. 383-389 (1981).
Y. Fulmer Shealy et al, J. Med. Chem., vol. 24, pp. 1083-1086 (1981).
Y. Fulmer Shealy et al, J. Heterocyclic Chem., vol. 17, pp. 353-358 (1980).
Y. Fulmer Shealy et al, J. Heterocyclic Chem., vol. 13, pp. 1015-1020 (1976).
Hronowski et al, Canadian J. Chem., vol. 63, No. 10, pp. 2787-2797 (1985).
Hronowski et al, Canadian J. Chem., vol. 64, No. 8, pp. 1620-1629 (1986).
STN Intl, File CA, Chemical Abstracts, vol. 107, No. 5, pp. 571-578 (1987).

*Primary Examiner*—John W. Rollins (Abstract continued on next page.)

Assistant Examiner—James O. Wilson
Attorney, Agent, or Firm—Birch, Stewart, Kolasch & Birch

[57] ABSTRACT

A compound of the formula

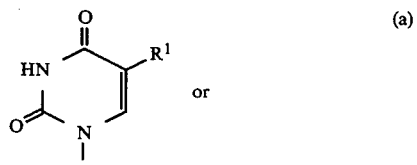

wherein the radicals A, X, $R^1$, $R^2$ and $R^3$ are defined as follows:

A:

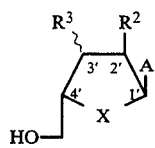

(a)

or

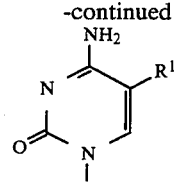

(b)

X: (a) O
   (b) S
   (c) $CH_2$ $R^1$: H; alkyl containing 1–3 carbon atoms;
—CH=$CH_2$; —CH=CH—$CH_3$; —$CH_2$—CH=$CH_2$;

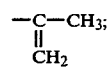

—C≡CH p1 $R^2$: H; or $R^2$ constitutes together with $R^3$ a carbon—carbon bond $R^3$: H; F; Cl; Br; I; $N_3$; CN; C≡CH; OH; $OCH_3$; $CH_2OH$; and when $R^3$ is F; Cl; Br; I; $N_3$; CN; C≡CH; OH; $OCH_3$ or $CH_2OH$ it may have either the cis-configuration or trans-configuration relative to the hydroxymetyl function at position 4', or $R^3$ constitutes together with $R^2$ a carbon—carbon bond, and therapeutically acceptable salts thereof, for use in therapy, in particular for the treatment of HIV virus infections.

1 Claim, No Drawings

α NUCLEOSIDE COMPOUNDS AND A METHOD FOR TREATING HBV USING SAID COMPOUNDS

This application is a continuation of application Ser. No. 07/794,704, now U.S. Pat. No. 5,215,970 filed on Nov. 20, 1991, which is a continuation application of Ser. No. 07/548,708, now abandoned, filed Jul. 6, 1990, which is a Continuation-in-Part application of Ser. No. 07/285,965, now abandoned, filed Dec. 12, 1988, the entire contents of which are hereby incorporated by reference.

FIELD OF THE INVENTION

The present invention relates to the use of chemical compounds and physiologically acceptable salts thereof for the therapheutic and prophylactic control and treatment of the Acquired Immuno Deficiency Syndrome (AIDS), infections by Human Immunodeficiency Virus, hepatitis B virus infections and retrovirus infections and method for such control and treatment in animal and man.

BACKGROUND OF THE INVENTION

In the late seventies a new disease was reported, which subsequently was referred to as Acquired Immuno Deficiency Syndrome (AIDS). It is now generally accepted that a retrovirus referred to as HIV (Human Immunodeficiency Virus), formerly known as Human T-cell Lymphotropic Virus (HTLV-III) or Lymphadenopathy Associated Virus (LAV) plays an essential role in the etiology of AIDS.

AIDS is characterized by a profound immunodeficiency due to low numbers of a subset of lymphocyte-T-helper cells, which are one target for HIV infection. The profound immunodeficiency in AIDS patients makes these patients highly susceptible to a variety of opportunistic infections of bacterial, fungal, protozoal or viral etiology. The etiological agents among viral opportunistic infections are often found in the herpes virus group, i.e., Herpes simplex virus (HSV), Varicella Zoster virus (VZV), Epstein-Barr virus (EBV) and, especially, cytomegalovirus (CMV). Other retroviruses affecting humans are HTLV-I and II and examples of retroviruses affecting animals are feline leukemia virus and equine infectios anaemia virus.

Hepatitis B virus infections cause severe disease such as acute hepatitis, chronic hepatitis, fulminant hepatitis in a considerable number of persons. It is estimated that there are 200 million patients with chronic hepatitis B infection in the world. A considerable number of the chronic cases progress to liver cirrhosis and liver tumours. In some cases the hepatitis infections also take a rapid and severe course as in fulminant B hepatitis with about 90% mortality. At present there is no known effective treatment against hepatitis B infections.

GENERAL OUTLINE OF THE INVENTION

A great number of nucleoside analogues exhibit several antimetabolic activities. They do so by substituting for or competing with the naturally occuring nucleosides. Recently some nucleoside analogues have been described, which inhibit in cell culture the multiplication of human immunodeficiency virus (HIV, also called HTLV-III, LAV), the causative agent of AIDS and AIDS-related complex (ARC). Such compounds are for example azidothymidine, dideoxycytidine and dideoxyadenosine. These and other described HIV-antimetabolic nucleoside analogues have the same geometric relationship between the nucleoside base and the glycosidic part as the naturally occuring nucleosides, i.e. they are β-anomers.

We have now, surprisingly, found that some nucleosides and nucleoside analogues with the opposite geometric configuration, α-anomers, are potent inhibitors of HIV multiplication but not of cell-division. Anti-HIV activities are displayed by such geometric isomers which have been modified either in the nucleoside base part, the glycoside part or in both parts. The structures of these compounds are disclosed in this invention.

PRIOR ART

The following compounds of the formula I below are known:
1. Compounds of the formula

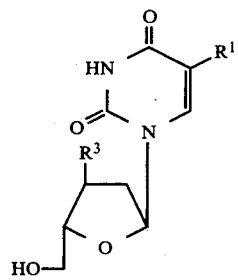

wherein $R^3$ is OH and $R^1$ is as follows:
- $R^1$ is H and $CH_3$: T. Nishimura, B. Shinizu, I. Iwai Chem. Pharm. Bull. (Tokyo) 12 (1964), 1471
- $R^1$ is $C_2H_5$: M. Swierkowski, D. Shugar J. Med. Chem. 12 (1969), 533
- $R^1$ is n—$C_3H_7$: A. Szaboles, J. Sági, L. Ötvös J. Carbohydrates, Nucleosides, Nucleotides 2 (1975), 197-211
- $R^1$ is i—$C_3H_7$: M. Draminski, A. Zgit-Wroblewska Polish J. Chemistry 54 (1980), 1085
- $R^1$ is C≡CH: P. J. Barr, A. S. Jones, P. Serafinowski, R. Walker J. Chem. Soc. Perkin I (1978), 1263-1267 and wherein $R^3$ is $N_3$ and $R^1$ is $CH_3$: M. Imezawa, F. Eckstein, J. Org. Chem. 43 (1978), 3044-3048.

2. The compound of the formula

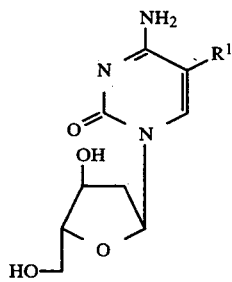

$R^1$ is C≡CH is described by P. J. Barr, A. S. Jones, P. Serafinowski, R. Walker, J. Chem. Soc. Perkin I (1978), 1263-1267

$R^1$ is H is described by J. J. Fox, N. C. Yung, I. Wempen and M. Hoffer, J. Am. Chem. Soc., Vol. 83 (1961), 4066-4070.

Both groups 1. and 2. concern only compounds having the 3'group and the 4'hydroxymethyl group in a trans-configuration.

DISCLOSURE OF THE INVENTION

It has been found according to the present invention that the compounds of the formula

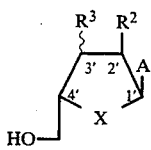

wherein the radicals A, X, $R^1$, $R^2$ and $R^3$ are defined as follows:

A:

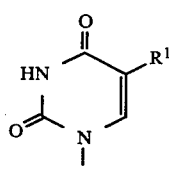

(a)

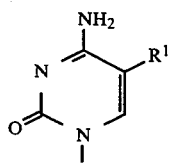

(b)

X: (a) O
 (b) S
 (c) $CH_2$ $R^1$: H; alkyl containing 1-3 carbon atoms; —CH=$CH_2$; —CH=CH—$CH_3$; —$CH_2$—CH=$CH_2$;

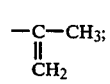

—C≡CH $R^2$: H; or $R^2$ constitutes together with $R^3$ a carbon—carbon bond $R^3$: H; F; Cl; Br; I; $N_3$; CN; —C≡CH; OH; $OCH_3$; $CH_2OH$; or $R^3$ constitutes together with $R^2$ a carbon—carbon bond, and therapeutically acceptable salts thereof, inhibit the multiplication of human immunodeficiency virus (HIV). The compounds of the formula I are useful as therapeutic and/or prophylactic agents in the control and treatment of HIV virus infections in mammals and man.

In a more general aspect, the compounds of the formula I are useful as therapeutic and/or prophylactic agents in the control and treatment of infections caused by retroviruses and hepatitis B virus in mammals and man.

All retroviruses, including HIV, require the enzyme reverse transcriptase in their natural cycle of replication.

Hepatitis B virus (HBV) is a DNA virus with a unique circular double-stranded DNA genome which is partly single-stranded. It contains a specific DNA polymerase required for vital replication. This DNA polymerase also acts as a reverse transcriptase during the replication of HBV DNA via an RNA intermediate.

The compounds of the formula I inhibit the activity of reverse transcriptase of retroviruses including HIV as well as the activity of DNA polymerase of hepatitis B virus.

The present invention has several aspects:

1. the novel compounds included in the formula I,
2. pharmaceutical compositions comprising a compound of the formula I as active ingredient,
3. a compound of the formula I for use in therapy,
4. a compound of the formula I for use in the manufacture of a medicament for therapeutic and/or prophylactic treatment of infections caused by a retrovirus, including HIV, or by hepatitis B virus,
5. a method for the therapeutic and/or prophylactic treatment of infections in mammals and man caused by retrovirus including HIV or hepatitis B virus, by administering to a host in need of such treatment an efficient amount of a compound of the formula I.

It is a preferred aspect of the invention to combat HIV virus infections in man.

The expression "alkyl containing 1-3 carbon atoms" for the radical $R^1$ means $CH_3$, $C_2H_5$, $CH_2CH_2CH_3$, $CH(CH_3)_2$ and cyclopropyl.

When $R^3$ in formula I is F, Cl, Br, I, $N_3$, CN, C≡CH, OH, $OCH_3$ or $CH_2OH$ it may have either cis-configuration or trans-configuration relative to the hydroxymethyl function at position 4'.

Preferred compounds of the formula I are:

(a) A is

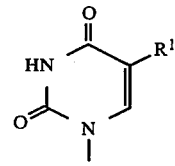

(b) A is

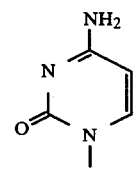

(c) $R^3$ at position 3' and the hydroxymethyl group at position 4' have the trans-configuration
(d) $R^1$ is $CH_3$ or $C_2H_5$
(e) X is O or $CH_2$
(f) X is O
(g) $R^2$ is H
(h) $R^2$ constitutes together with $R^3$ a carbon—carbon bond
(i) $R^3$ is H, F, $N_3$, OH, $OCH_3$, or $CH_2OH$ or constitutes together with $R^2$ a carbon—carbon bond
(j) $R^3$ is H, F, or $N_3$
(k) the combination of (a), (c), (d) and (e) above
(l) the combination of (a), (c), (d), (e), (g) and (i) above
(m) the combination of (a), (c), (d), (f), (g) and (j) above
(n) the combination (a), (c), (d), (e) and (h) above
(o) the combination (b), (c), (d) and (e) above (p) the combination (b), (c), (d), (e), (g) and (i) above
(q) the combination (b), (c), (d), (f), (g) and (j) above
(r) the combination (b), (c), (d), (e) and (h) above Examples of preferred compounds are:

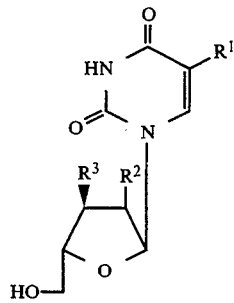

$R^1$ is $CH_3$; $R^2$ is H; $R^3$ is H
$R^1$ is $CH_3$; $R^2$ is H; $R^3$ is OH
$R^1$ is $CH_3$; $R^2$ is H; $R^3$ is $OCH_3$
$R^1$ is $CH_3$; $R^2$ is H; $R^3$ is $CH_2OH$
$R^1$ is $CH_3$; $R^2$ is H; $R^3$ is F
$R^1$ is $CH_3$; $R^2$ is H; $R^3$ is $N_3$
$R^1$ is $CH_3$; and $R^3$ constitute together a carbon—carbon bond
$R^1$ is $C_2H_5$; $R^2$ is H; $R^3$ is H
$R^1$ is $C_2H_5$; $R^2$ is H; $R^3$ is OH
$R^1$ is $C_2H_5$; $R^2$ is H; $R^3$ is $OCH_3$
$R^1$ is $C_2H_5$; $R^2$ is H; $R^3$ is $CH_2OH$
$R^1$ is $C_2H_5$; $R^2$ is H; $R^3$ is F
$R^1$ is $C_2H_5$; $R^2$ is H; $R^3$ is $N_3$
$R^1$ is $C_2H_5$; $R^2$ and $R^3$ constitute together a carbon—carbon bond

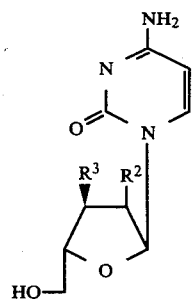

$R^2$ is H; $R^3$ is H
$R^2$ is H; $R^3$ is OH
$R^2$ is H; $R^3$ is $OCH_3$
$R^2$ is H; $R^3$ is $CH_2OH$
$R^2$ is H; $R^3$ is F
$R^2$ is H; $R^3$ is $N_3$
$R^2$ and $R^3$ constitute together a chemical bond In all the examples of preferred compounds $R^3$ at position 3' and hydroxymethyl at position 4' have the trans-configuration.

In clinical practice the nucleosides of the formula I will normally be administered orally, by injection or by infusion in the form of a pharmaceutical preparation comprising the active ingredient in the form of the original compound or optionally in the form of a pharmaceutically acceptable salt thereof, in association with a pharmaceutically acceptable carrier which may be a solid, semi-solid or liquid diluent or an ingestible capsule. The compound may also be used without carrier material. As examples of pharmaceutical preparations may be mentioned tablets, dragées, capsules, granulates, suspensions, elixirs, syrups, solutions etc. Usually the active substance will comprise between 0.05 and 20% for preparations intended for injection and between 10 and 90% for preparations intended for oral administration.

In the treatment of patients suffering from retrovirus, especially HIV, or hepatitis B virus infections, it will be preferred to administer the compounds by any suitable route including the oral, parenteral, rectal, nasal, topical and vaginal route. The parenteral route includes subcutaneous, intramuscular, intravenous and sublingual administration. The topical route includes buccal and sublingual administration. The dosage at which the active ingredients are administered may vary within a wide range and will depend on various factors such as the severity of the infection, the age of patient etc., and may have to be individually adjusted. As a possible range for the amount of the compounds of the invention or a physiologically acceptable salt thereof to be administered per day may be mentioned from about 10 mg to about 10 000 mg, preferentially 100–500 mg for intravenous administration and preferentially 100–3000 mg for oral administration.

Examples of pharmaceutically acceptable salts of the compounds of formula I include base salts, e.g. derived from an appropriate base, such as alkali metal (e.g. sodium), alkaline earth metal (e.g. magnesium) salts ammonium and $NX_4^+$ (wherein X is $C_{1-4}$ alkyl) Physiologically acceptable salts of a hydrogen atom or an amino group include salts of organic carboxylic acids such as acetic, lactic, gluconic, citric, tartaric, maleic, malic, panthothenic, isethionic, succinic, oxalic, lactobionic and succinic acids; organic sulfonic acids such as methanesulfonic, ethanesulfonic, benzenesulfonic, p-chlorobenzenesulphonic and p-toluenesulfonic acids and inorganic acids such as hydrochloric, hydroiodic, sulfuric, phosphoric and sulfamic acids. Physiologically acceptable salts of a compound of an hydroxy group include the anion of said compound in combination with a suitable cation such as $Na^+$, $NH_4^+$, and $NX_4^+$ (wherein X is a $C_{1-4}$ alkyl group).

Those compounds of the formula I which are novel are summarized as compounds of the formula I with the provisos that 1. when A, X, $R^2$ and $R^3$ are combined as follows:

A is

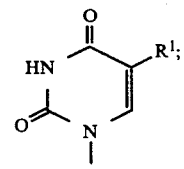

X is O;
$R^2$ is H;
$R^3$ is OH;
then $R^1$ is $-CH=CH_2$, $-CH=CH-CH_3$, $-CH_2-CH=CH_2$,

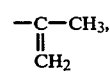

or cyclopropyl;

2. when A, X, $R^2$ and $R^3$ are combined as follows:

A is

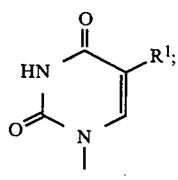

X is O;
R² is H;
R³ is N₃;
then R¹ is H; alkyl containing 2-3 carbon atoms, —CH=CH₂; —CH=CH—CH₃; —CH₂—CH=CH₂;

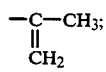

—C≡CH; or cyclopropyl;
3. when A, X, R² and R³ are combined as follows:
A is

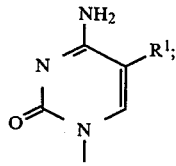

X is O;
R² is H;
R³ is OH;
then R¹ is alkyl containing 1-3 carbon atoms, —CH=CH₂; —CH=CH—CH₃; —CH₂—CH=CH₂;

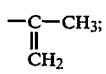

or cyclopropyl.

The administered compounds may also be used in therapy in conjunction with other medicaments such as 9[(2-hydroxy-1-(hydroxymethyl)ethoxy)-methyl]guanine, 9-(2-hydroxyethoxymethyl)guanine (acyclovir), 2-amino9-(2-hydroxyethoxymethyl)purine, interferon, e.g., α-interferon, interleukin II, and phosphonoformate, or in conjunction with immune modulating therapy including bone marrow or lymphocyte transplants or medications such as levamisol or thymosin which would increase lymphocyte numbers and/or function as is appropriate.

METHODS OF PREPARATION

The compounds of the invention may be prepared by one of the following general methods, constituting a further aspect of the invention.

A. Condensing a glycoside as comprised in formula I, where the hydroxyl groups may be optionally protected, to the N-1 position of a pyrimidine derivative, corresponding to radical A in formula I according to known methods described in the literature, followed by separation of the α-anomer and removal of any protecting group(s). Such methods are described for example in "Basic Principles in Nucleic Acid Chemistry", Vol. 1 (Academic Press, 1974, Ed. P.O.P.Ts'o), in "Nucleoside Analogues, Chemistry, Biology and Medical Applications" (Pharma Press, 1979, Eds. R. T. Walker, E. De Clercq and F. Eckstein) and in Nucleic Acids Research Vol. 12, 1984, pages 6827–6837 (A. J. Hubbard, A. S. Jones and R. T. Walker). An example of such a method is given for the case of a uracil base analogue:

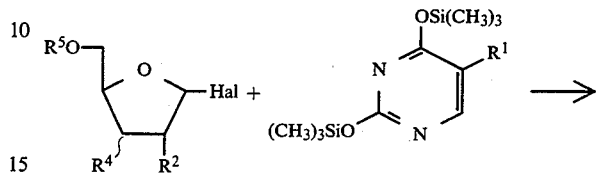

wherein R⁴ is H, F, Cl, Br, I, N₃, CN, C≡CH, OR⁵, OCH₃ or CH₂OR⁵, R⁵ is a protecting group, of which a great variety is known, and examples of which are p-toluoyl, acetyl, trityl, benzyl. R¹ and R² are as defined above.

B. Anomerization of a β-anomer of the formula

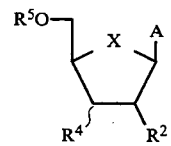

wherein A, X, and R² are as defined above, R⁴ is H; F; Cl; Br; I; N₃; CN; OR⁵; OCH₃; or CH₂OR₅; wherein R⁵ is H or a hydroxy-protecting group to a mixture of α- and β-anomers, whereafter the α-anomer is separated and any protecting groups removed. The anomerization may be performed by known methods, e.g. with an optionally protected β-nucleoside, for example a silylated nucleoside, with a catalyst, such as for example trimethylsilyl trifluoromethanesulfonate

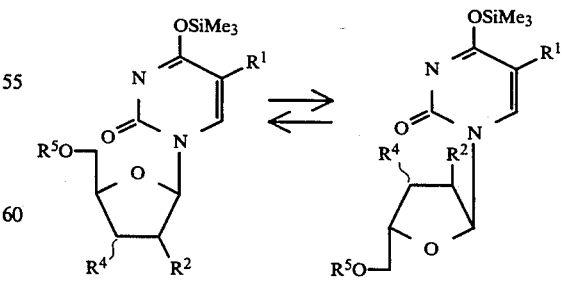

R¹, R², R⁴ and R⁵ are as defined above.

C. A transglycosylation reaction whereby the sugar moiety forming a bond, α- or β-, to one nucleoside base, is transferred to the desired pyrimidine base. The reaction is performed with a catalyst such as for example trimethylsilyl trifluoromethanesulfonate, and is followed by separation of the products and deprotection.

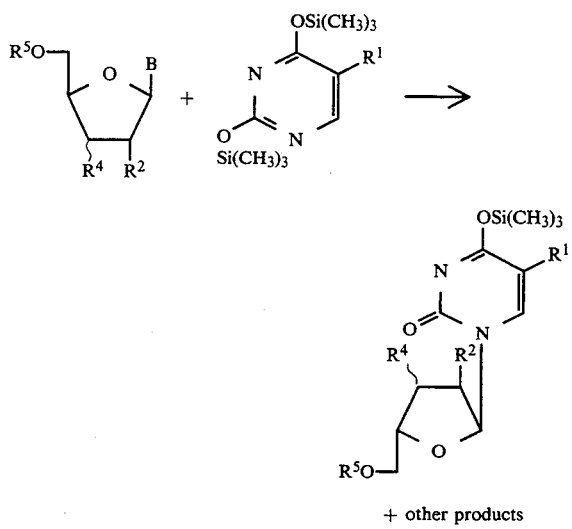

+ other products wherein $R^1$, $R^2$, $R^4$ and $R^5$ are as defined above. The radical B is a pyrimidine or purin base, the choice of which is not critical.

D. Introduction of the functional group $R^3$, or a precursor of $R^3$, into the nucteoside α-anomer by substitution of a suitable leaving group, $R^7$, followed by deprotection.

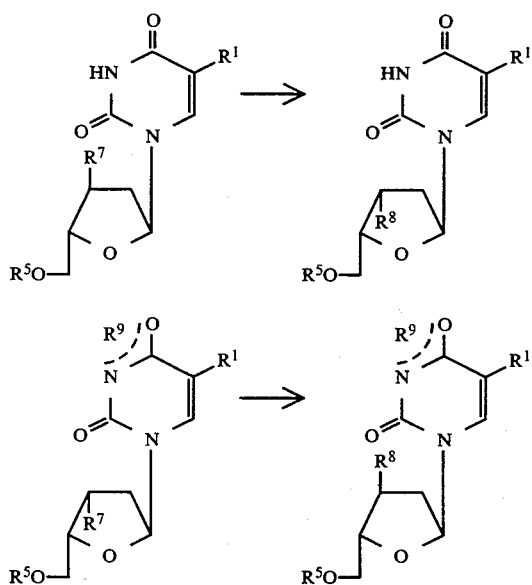

$R^1$ and $R^5$ are as defined above, $R^7$ is a good leaving group such as for example trifluoromethanesulfonyloxy, $R^8$ is F, Cl, Br, I, $N_3$, CN, $OCH_3$ and synthos for the C≡CH, OH and $CH_2OH$ groups, such as for example C≡C—Si(CH$_3$)$_3$, $CH_3CO_2$ and

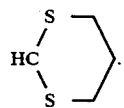

$R^9$ is a suitable protecting group.

An alternative way for introduction of the $R^8$ function is by reaction of the 2,3'-anhydro α-anomer.

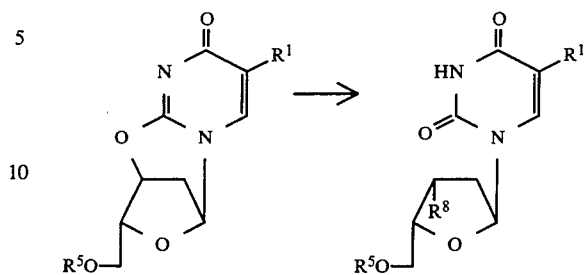

wherein $R^1$, $R^5$ and $R^8$ are as defined above.

The principles of methods A–D above are applicable to the synthesis of both uridine and cytidine analogues of formulas I and II, although the formulas illustrating the reactions only depict uridine analogues.

E. Converting the uracil moiety of the 5-substituted or unsubstituted α-uridine compounds to a cytosine moiety of the corresponding α-cytidine analogues. This is carried out by conventional methods, the principles of which have been described for example by W. L. Sung (J. Chem. Soc. Chem. Comun. 1981, p. 1089 and J. Organic Chemistry 1982, volume 47, pages 3623–3628) and by P. Herdewijn et al. (J. Medicinal Chemistry 1985, volume 28, pages 550–555).

The following examples will further illustrate the invention.

PREPARATION OF INTERMEDIATE PRODUCTS

A. Preparation of 3'F-3'-deoxy-5'-O-acetylthymidine (VSB423)

3'F-3'-deoxythymidine 45 mg (0.184 mmol) in acetic anhydride (2.0 mL) was heated with stirring in an oil bath at 80° for 7 hrs. The solution was evaporated in vacuo and the residual acetic anhydride and acetic acid were removed by several additions and reevaporations with benzene-toluene (1:1). The residue was used without further purifications.

PREPARATION OF COMPOUNDS OF THE INVENTION

Example 1

Preparation of 1-(3-F-2,3-dideoxy-α-D-ribofuranosyl)thymine (VSA 419) (Method B)

Thymine 23 mg (0.18 mmol) and 3'F-3'-deoxy-5'-O'-acetylthymidine was suspended in acetonitrile (1.2 mL) and N,O-Bis (trimethylsilyl)-acetamide (0.35 mL) was added. The mixture was stirred at room temperature for 1.5 hrs. Trimethylsilyl trifluoromethanesulfonate (0.05 mL) was added. After stirring at room temperature for 192 hrs, the mixture was poured under stirring into a 1:1 (v/v) mixture of 20 ml of 10% aqueous KHCO$_3$-ethyl acetate. Two phases were separated and the water phase was extracted with ethyl acetate (3×10 mL). The combined ethyl acetate phase was filtered and evaporated in vacuo. The residue was dissolved in dichloromethane-ethyl acetate 1:1 and applied to a column of silica gel, and the column was eluated with dichloromethane-ethyl acetate 1:1 to give 28 mg (53%) starting material (VSB 423) (Rf 0.37 on TLC silicagel CH$_2$Cl$_2$-EtoAc 1:1) and 18 mg (34%) of 1-(3-F-2,3- dideoxy-5-O-acetyl-α-D-ribofuranosyl)thymine (VSB 424) (Rf 0.29 on TLC silica gel CH$_2$Cl$_2$-EtoAc 1:1).

NMR (CD$_3$OD) δ1.95 (s, 3H, CH$_3$-5), 2.12 (s, 3H, CH$_3$CO), 2.3–3.0 (m, 2H, H-2'a,b), 4.15 (d, 2H, J4', 5'=4.4 Hz, H-5'a,b) 4.81 (dt 1H, J3'F,4'=30.0 Hz, J4', 5'=4.6 Hz H-4') 5.23 (dd, 1H, J3'F, 4'=30.0 Hz, J4',5'=4.6 Hz, H-4'), 5.23 (dd, 1H, J3'F, 3'=53.7 Hz, J2',3'=5.0 H-3'), 6.36 (d, 1H, J',2'=7.57 Hz, H-1'), 7.27 (d, 1H, J H-6, CH$_3$=1.47, H-6)

$^{13}$C(CD$_3$OD) δ12.80 (CH$_3$), 20.87 (CH$_3$CO), 39.40 (d, J=20.8 Hz, C-2'), 63.37 (d, J=12.2 Hz, C-5'), 84.65 (d, J=24.4 Hz, C-4'), 86.50 (s, C-1') 93.82 (d, J=178 Hz, C-3'), 111.12 (C-5), 135.07 (d, J=6.1 Hz, C-6), 150.48 (C-2), 163.68 (C-4), 170.30 (CH$_3$CO).

The compound VSB 424 (16 mg) was dissolved in saturated methanolic ammonia (5 mL) and left at room temperature overnight. The solution was evaporated and the residue was treated with acetone-benzene (1:4) to give crystals of the desired compound, VSA 419 (9.4 mg, 69%) UV λmax (H$_2$O) 269 nm.

NMR (DMSO-d6) $^1$H δ1.79 (d, 3H, J CH$_3$, H-6=1.2 Hz CH$_3$), 2.16–2.90 (m, 2H, H-2'), 3.2–3.6 (m, 2H, H-5'), 4.61 (dt, 1H, J3'F,4'=23.4 Hz, J4',5'=~4 Hz, H-4'), 5.06 (t, 1H, J5',OH=5.6 Hz, OH), 5.32 (dd, 1H, J3'F,3'=54.2 Hz J2'3'=4.9 Hz, H-3'), 6.18 (dd, 1H, J1'2'=7.7 Hz and 2.1 Hz, H-1'), 7.39 (d, 1H, J CH$_3$, H-6=1.2 Hz, H-6) $^{13}$C (DMSO-d6) δ12.46 (CH$_3$), ~39 (C-2'), 61.17 (d, J=11.0 Hz, C-5'), 85.85 (C-1'), 87.15 (d, J=20.8 Hz, C-4'), 94.75 (d, J=173 Hz, C-3'), 109.15 (C-5), 135.63 (d, J=6.1 Hz, C-6), 150.53 (C-2), 163.95 (C-4)

Example 2

Preparation of 1-(3-F-2,3-dideoxy-α-D-ribofuranosyl)-5-propyluracil (VSA 409) (Method C)

5-Propyluracil (56 mg) and 3'-F-3'deoxythymidine (47 mg) were suspended in acetonitrile (1.2 mL) and N,O-Bis (trimethylsilyl) acetamide (0.35 mL) was added. The mixture was stirred at room temperature for 1.5 hrs. Trimethylsilyl trifluoromethanesulfonate (0.05 mL) was added. After stirring at room temperature for 138 hrs, the mixture was evaporated in vacuo and added to H$_2$O (0.5 mL), filtered and washed with H$_2$O (0.5 mL). The combined water phase was applied to a C$_{18}$-column (HPLC) and eluted with methanol-water (35:65), at a rate of 7.0 ml/min. The β-anomer eluted after 12.9 min, and the desired α-anomer, VSA 409, after 18.0 min. Yield 9.3 mg (18%), UV λmax (H$_2$O) 269 nm, MS M+272 (10%), 154 (100%), 119 (76%).

Example 3

Preparation of 1-(3-F-2,3-dideoxy-α-D-ribofuranosyl)-5-ethyluracil (VSA 411) (Method C)

5-Ethyluracil (51 mg) and 3'F-3'-deoxythymidine (48 mg) were suspended in acetonitrile (1.2 mL) and N,O-Bis (trimethylsilyl) acetamide (0.35 mL) was added. The mixture was stirred at room temperature for 1.5 hrs. Trimethylsilyl trifluoromethanesulfonate (0.05 mL) was added. After stirring at room temperature for 161 hrs, the mixture was evaporated in vacuo, and added to water (0.5 mL), filtered and washed with water (0.5 mL). The combined water phase was applied to a C$_{18}$-column (HPLC) and eluted with methanol-water (1:3) at a rate of 8.0 ml/min. The β-anomer eluted after 12.3 min and the desired α-anomer, VSA 411, after 16.4 min.

Yield 13.1 mg (26%). UV λmax (H$_2$O) 267.5 nm. MS M+258 (9%), 140 (100%), 119 (67%).

Example 4

Preparation of 1-(2-deoxy-α-D-ribofuranosyl)-5-isopropenyluracil (VSA 175) (Method A)

5-Isopropenyluracil (4.3 g), hexamethyldisilazane (50 ml), chlorotrimethylsilane (1 ml) and ammoniumsulfate (catalytic amount) were heated at reflux for 2.5 hrs. Excess of solvent was evaporated in vacuo and the residual bis-silylated 5-isopropenyluracil (8.4 g) was dissolved in dichloroethane (50 ml) and added to 2-deoxy-3,5-di-O-p-toluoyl-D-erythro-pentosyl chloride (11.0 g) in dichloroethane (150 ml) also containing molecular sieves (4 Å, 15 g). The suspension was stirred at room temperature overnight, after which it was filtered and the solvent was evaporated. The residue was redissolved in dichloromethane which was washed with saturated aq NaHCO$_3$ and H$_2$O, dried over Na$_2$SO$_4$ and concentrated to a volume of about 70 ml. A precipitate formed which was filtered off, dichloromethane was evaporated from the filtrate and the residue was subjected to chromatography on silica gel columns eluted with hexane/ethylacetate/dichloromethane (5/5/3), to give 1-(2-deoxy-3,5-di-O-p-toluoyl-α-D-ribofuranosyl)-5-isopropenyluracil (VSA 174), 2.64 g (Thin layer chromatography, silica gel, solvent system as above, Rf=0.5).

Sodium metal (0.25 g) was dissolved in dry methanol (263 ml), compound VSA 174 (2.64 g) was added and the solution was stirred at room temperature overnight, after which water (35 ml) was added. The solution was neutralized with an ion exchanger (Dowex H+50Wx2), filtered and the solvent was evaporated. The residue was washed with hexane and purified by chromatography on a column of silica RP18 eluted with 50% aq methanol to give 1-(2-deoxy-α-D-ribofuranosyl)-5-isopropenyluracil. (TLC silica RP8, 50% aq methanol, Rf=0.5).

Scheme for synthesis of the compounds wherein X = CH$_2$

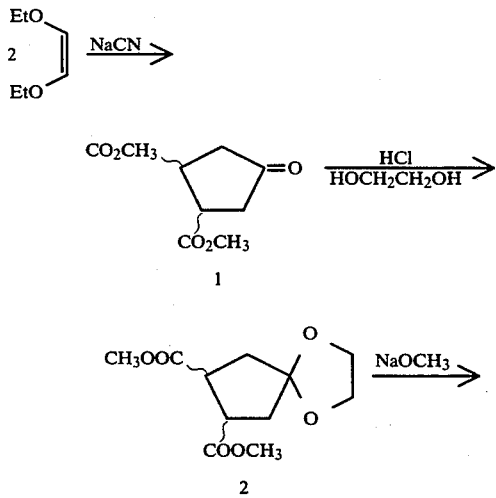

-continued
Scheme for synthesis of the compounds wherein X = CH₂
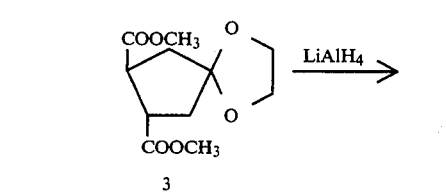
3
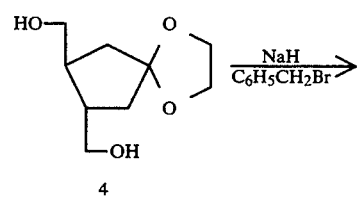
4
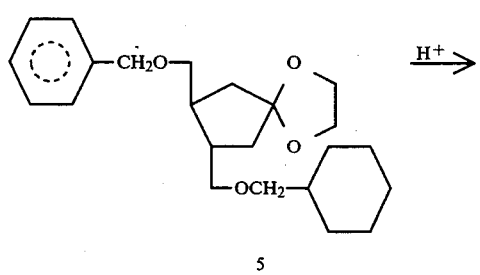
5
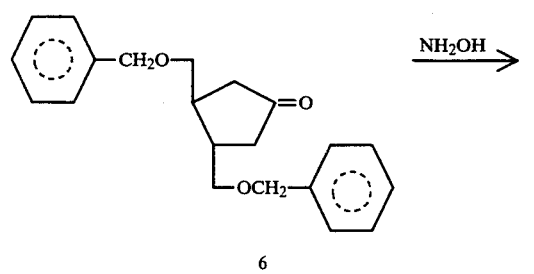
6
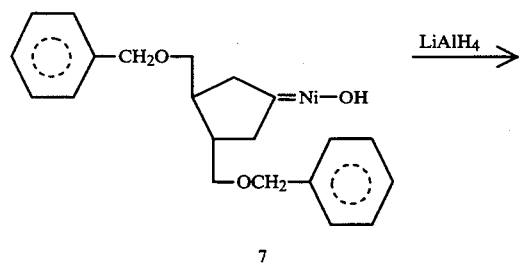
7
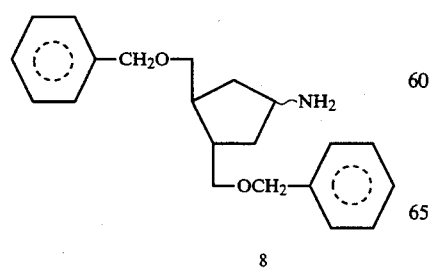
8
-continued
Scheme for synthesis of the compounds wherein X = CH₂
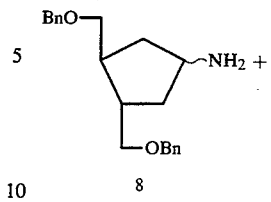
8
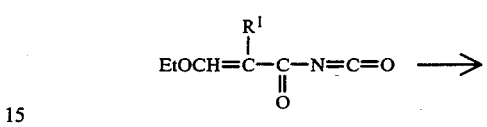
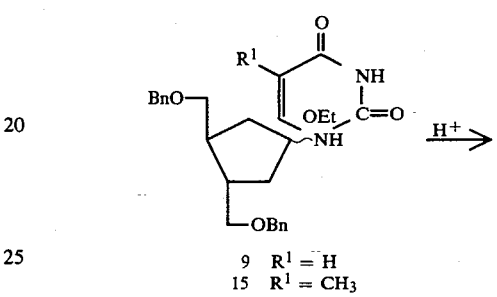
9  R¹ = H
15 R¹ = CH₃
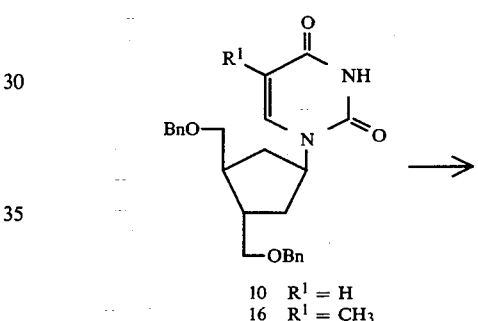
10 R¹ = H
16 R¹ = CH₃
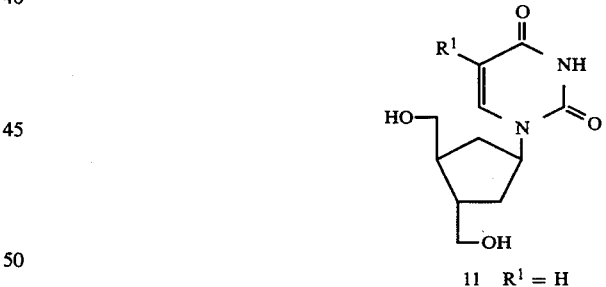
11 R¹ = H
17 R¹ = CH₃
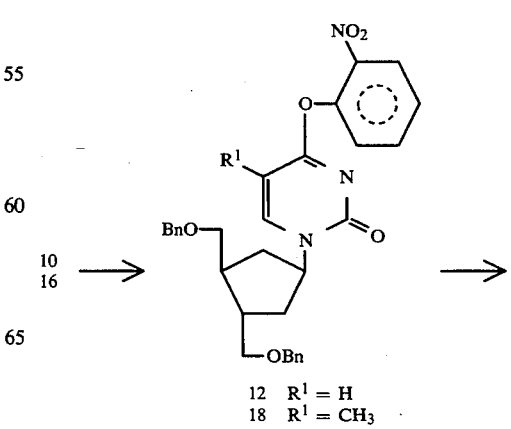
12 R¹ = H
18 R¹ = CH₃

-continued
Scheme for synthesis of the compounds wherein X = CH₂

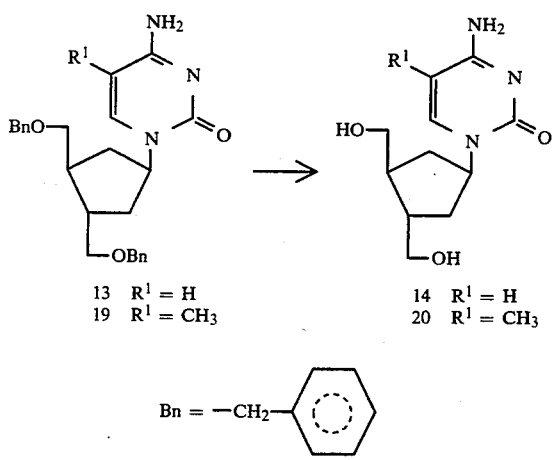

13 R¹ = H
19 R¹ = CH₃

14 R¹ = H
20 R¹ = CH₃

Bn = —CH₂—⟨ ⟩

PREPARATIONS OF COMPOUNDS OF THE INVENTION

Example 5

Preparation of 1-[2',3'-Dideoxy-3'-C-(hydroxymethyl)-α-D-erythropentofuranosyl]-cytosine (compound 21)

A suspension of cytosine (120 mg, 1.08 mmol) and a small crystall of (NH₄)₂SO₄ in hexamethyldisilazane (2 ml) and trimethylchlorosilane (0.2 ml) was refluxed until a clear solution was obtained. The solution was concentrated in vacuo and co-evaporated with dry xylene. The solid residue was dissolved in dry CH₂Cl₂ (2 ml) under nitrogen and methyl-5-O-benzoyl-3-[(benzoyloxy)methyl]-2,3-dideoxy-D-erythro-pentofuranoside (170 mg, 0.46 mmol) was added followed by the addition of t-butyldimethylsilyl-triflate (0.22 ml, 0.96 mmol). After 24 h at room temperature the reaction was quenched by the addition of aqueous NaHCO₃ (sat.) and the resulting mixture was stirred for 30 minutes. The solution was diluted with CH₂Cl₂ and washed with NaHCO₃ (sat.), dried, filtered and concentrated to give an anomeric mixture of the protected nucleoside. This mixture was treated with methanolic ammonia (20 ml, sat.) for 24 h at room temperature, After concentration, the residue was dissolved in water and extracted with CH₂Cl₂. The aqueous phase was concentrated to a small volume and was applied to a semi-preparative C-18 reversed phase chromatography column and eluted with water containing 2% methanol. First the α-isomer was collected, followed by the β-isomer. The appropriate fractions were combined and evaporated to give 33 mg of the ci-anomer (30%) and 27 mg of the β-anomer (24%). α-Anomer: $[\alpha]^{26}D$: −54° (c 0.3, H₂O); UV (H₂O) $\lambda_{max}$:272 nm (ε10894); ¹H-NMR (270 MHz, D₂O): 1.92 (m,$J_{2'a,2'b}$=13.5 Hz, $J_{2'a,3'}$=9 Hz, $J_{2'a,1'}$=6.5 Hz, 1H, H-2'a); 2.5 (m, 1H, H-3'); 2.7 (m, $J_{2'a,2'b}$=13.5 Hz, $J_{2'a,3'}$=8 H2, $J_{2'a,1'}$=6 Hz, 1H, H-2'b); 3.67, 3.69 (d and q, overlapping, $J_{6',3'}$=6.2 Hz, $J_{5'a,5'b}$=12.5 Hz, $J_{4',5'a}$=5.3 Hz, 3H, H-6' and H-5'a); 3.85 (q, $J_{5'a,5'b}$=12.5 Hz, $J_{4',5'b}$=3 Hz, 1H, H-5'b); 4.28 (m, $J_{3',4'}$=8 Hz, $J_{4',5'a}$=5.3 Hz, $J_{4',5'b}$=3 Hz, 1H, H-4'); 6.1 (d and q, overlapping, $J_{5,6}$=7.3 Hz, $J_{1',2'}$=6.5 Hz, 2H, H-5 and H-1'); 7.8 (d, $J_{5,6}$=7.3 Hz, 1H, H-6); ¹³C-NMR (25.05 MHz, D₂O): 36.4 (C-2'); 42.3 (C-3'); 62.7, 63.6 (C-5',C-6'); 84.4, 88.2 (C-1', C-4'); 96.6 (C-5); 141.9 (C-6); 158.1 (C-2); 166.8 (C-4).

Example 6

Preparation of 1-[2',3'-Dideoxy-3'-C-(hydroxymethyl)-α-D-erythropentofuranosyl]-thymine (compound 22)

Thymine (150 mg, 1.19 mmol) was condensed with methyl 3-C-[(benzoyloxy)methyl]-5-O-p-bromobenzyl-2,3-dideoxy-D-erythro-pentofuranoside (205 mg, 0.47 mmol) following the same procedure as described in Examples 1 and 2 to give an anomeric mixture of the protected nucleoside. The mixture was dissolved in ethanol containing NaHCO₃ (excess) and was hydrogenated over Pd (10% on carbon, 1 atm) for 3 hours. After workup the residue was further reacted with methanolic ammonia for 24 hors. After concentration the residue was dissolved in water and extracted with CH₂Cl₂. The aqueous layer was concentrated to a small volume and was subjected to semi-preparative C-18 reversed phase column chromatography and eluded with water containing 10% methanol. First the α-isomer was eluted, followed by the β-isomer. The appropriate fractions were combined and evaporated to give 40 mg of the α-anomer (33%) and 41 mg of β-anomer (33%).

α-Isomer: $[\alpha]^{26}D$: −3.6° (c 0.36, H₂O); UV (H₂O) $\lambda_{max}$:268 nm (ε13756); ¹H-NMR (270 MHz, D₂O): 1.89 (d, J=1.1 Hz, 3H, 5-CH₃); 1.96 (m, $J_{2'a,2'b'}$=13.2 Hz, $J_{2'a,3'}$=9.9 Hz, $J_{2'a,1'}$=7.7 Hz, 1H, H-2'a); 2.47 (m, 1H, H-3'); 2.6 (m, $J_{2'a,2'b'}$=13.2 Hz, $J_{2'b,3'}$=8.1 Hz, $J_{2'b,1'}$=6.2 Hz, 1H, H-2'b); 3.64 and 3.68 (d and q overlapping, $J_{5'a,4'}$=5.5 Hz, $J_{5'a,5'b}$=12.1 Hz, $J_{6',3'}$=6.1 Hz, 3H, H-5'a, H-6'); 3.81 (q, $J_{5'b,4'}$=2.9 Hz, $J_{5'b,5'a}$=12.1 Hz, H-5'b); 4.24 (m, $J_{3',4'}$=8.4 Hz, $J_{4',5'a}$=5.5 Hz, $J_{4',5'b}$=2.9 Hz, 1H, H-4); 6.11 (q, $J_{1',2'a}$=7.7 Hz, $J_{1'2'b}$=6.2 Hz, 1H, H-1'); 7.59 (d, J=1.1 Hz, 1H, H-6); ¹³C-NMR (25.05 MHz, D₂O): 12.5 (5-CH₃); 35.7 (C-2'); 42.7 (C-3'); 62.6, 63.5 (C-5', C-6'); 84.2, 87.3 (C-1', C-4'); 111.6 (C-5); 138.1 (C-6); 152.4 (C-2); 167.3 (C-4).

Example 7

Preparation of 1-[(3,4-trans-C-dihydroxymethyl)cyclopentyl]uracil (compound 11)

The 3,4-Dibensylcyklamin (1.0 g, 3.1 mmol) (compound 8) was dissolved in 10 ml C₆H₆ under nitrogen. C-Ethoxyacryloylisocyanate (Y. F. Sheely, J. Heterpcycl. Chem. 1976, Vol 13, p. 1015) (0.38M in C₆H₆, 8.2 ml, 3.1 mmol) was added at 20° C. and with vigorous stirring. After a reaction time for 20 minutes the solution was evaporated and the residue was dissolved in trifluoroacetic acid (20 ml, 70% aqeous). The solution was refluxed for 30 minutes, the solution was cooled and diluted with H₂O (50 ml) and extracted with Et₂O/-Toluene 1:1. The organic phase was washed with H₂O (3×50 ml) and dried with Na₂SO₄ and NaHCO₃.

Filtration and evaporation gave a pale brown gum of 1-[(3,4-trans-C-dibensylomethyl)cyclopentyl]uracil (compound 10). This gum was dissolved in CH₂Cl₂ (5 ml) under nitrogen and was treated with trimethylsilyl iodide (0.72 ml, 5.11 mmol). The resulting cloudy yellow solution was stirred at 20° C. for 60 minutes. The solution was evaporated, dissolved in CH₂Cl₂ and extracted with H₂O (8×2 ml). The aqeous phase was washed with Et₂O (3×5 ml) and evaporated).

Final purification was made by flash-chromatography (Merck Si 60) elution with etylacetate 7-methanol 1-H$_2$O 0.5. Evaporation of the pure fractions gave the title compound as a colourless gum.

$^1$H-NMR Bruker 250 MHz, D$_2$O; 1.5–2.4 ppm—CH$_2$CHN, 4H, CHCH$_2$O, 2H. 3.4–3.8 ppm (CH$_2$O, 4H (m) 4.7–4.9 ppm. CHN, 1H, 5.8–5.9 ppm (CH=CH, 1H (d) 7.7–7.8 ppm CH=CH1H (d).

Example 8

Preparation of 1-[(3,4trans-C-dihydroxymethyl-)cyclopentyl]uracil (compound 17)

The compound was prepared by the procedure described for compound 11 in Example 7, substituting methoxymetacryloyl-isocyanate (prepared according to G. Shaw and R. N. Warrener, J. Chem. Soc. 1958, p. 157) for ethoxyacryloyl isocyanate.

$^1$H NMR Bruker 250 MHz D$_2$O; 1.87 ppm—CH$_3$ (d)3H, 1.9–2.3 CH$_2$CHN (m) 4H, 3.5–3.7 CH$_2$OH (m) 4H, 4.7–4.9 CHN (m), 7.57 CH=C (s), 1H.

Example 9

Preparation of 1-[3,4-trans-C-dihydroxymethyl(cyclopentyl]cytosine (compound 14)

1-[(3,4-trans-C-Dibensyloxymethyl)cyclopentyl-]uracil (compound 10, obtained as described in Example 7), 0.5 g, 1.9 mmol was dissolved in CH$_2$H$_2$ (20 ml) and triethylamine (0.31 ml, 3 mmol), mesitylensulfonylchloride (0.33 g, 1.5 mmol) and dimethylaminopyridine (0.037 g, 0.3 mmol) were added under a nitrogen athmosphere and vigorous stirring. The solution was stirred at 40° C. for 2 hours and 2-nitrophenol (0.67 g, 5.0 mmol) was added together with triethylamine (0.50 ml, 3.6 mmol). The solution was stirred over night. Diethylether (50 ml) was added and the solution was washed with 0.5N NaOH (3×20 ml). The organic phase was dried with Na$_2$SO$_4$ and evaporated. The residue was purified by flash-chromatography on silica gel (Merck Si 60) (elution with EtoAc/cyklohexane 1:1). The pure fractions were collected and evaporated to give a colourless gum, The gum was dissolved in THF (5 ml) and NH$_4$OH aq (25%, 2 ml) was added and the mixture was stirred at 0.5 bar and 65° C. over night. The solution was evaporated and the residue was purified on silica gel by elution with ethylacetate/methanol 8:1. Evaporation of the pure fractions gave a gum.

The gum was dissolved in CH$_2$Cl$_2$ (1 ml) and trimethylsilyl iodide (0.018 ml, 0.125 mmol) was added under nitrogen. The solution was stirred for 60 minutes at 20° C. and evaporated.

The residue was dissolved in H$_2$O (1 ml) and washed with Et$_2$O (2×2 ml). The aqeous phase was evaporated to give the title compound as a white solide.

$^1$H-NMR Bruker 250 MHz D$_2$O 20 C.: 1.4–2.4 ppm (CH$_2$CHN, CHCH$_2$O (m) 6H 3.4–3.8 ppm CH$_2$OH (m) 4H 4.6–4.8 (CHN) (m) 1H 5.8–5.9 ppm CH=CH (d) 1H 7.7–7.8 CH=CH (d) 1H.

Example 10

Preparation of 1-[(3,4-trans-C-dihydroxymethyl)cyclopentyl]-5-methylcytosine (compound 20)

The title compound was prepared from 1-[(3,4-trans-C-dibensyloxymethyl)-cyclopentyl]thymine (compound 16) in the same manner as described for compound 14 in Example 9.

PREPARATION OF INTERMEDIATE PRODUCTS

The starting materials for the compounds 21 and 22 in Examples 5 and 6 respectively were prepared by the following sequence of reactions a–d:

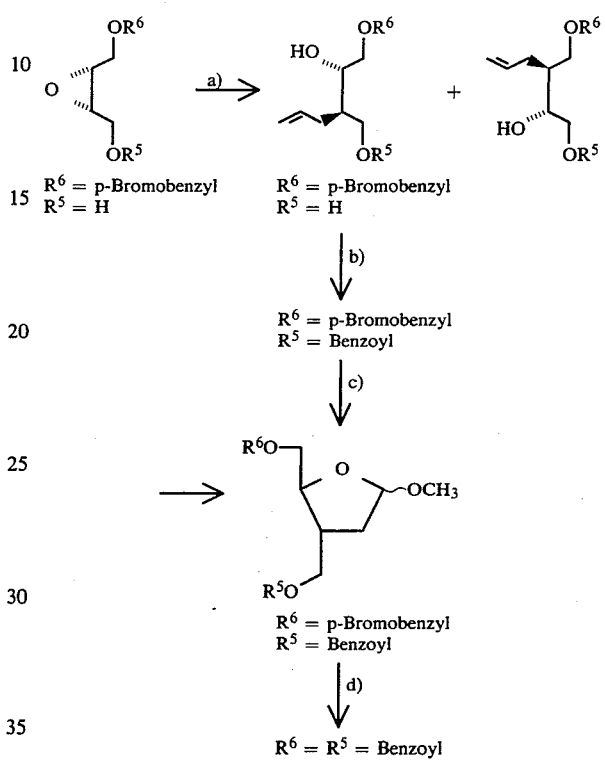

a) (2S,3R)-1-O-P-Bromobenzyl-3-C-(2'-propenyl)-1,2,4-butantriol. To a cold solution of allylmagnesium bromide −50° C. (20 ml, 1M) in 100 ml of dry diethyl ether Under nitrogen atomosphere, a solution of (2S,3R)-3-[[(4-bromobenzyl)oxy]methyl]oxirane-2-methanol-1 (1.36 g, 5 mmol) in 140 ml of dry diethyl ether was added dropwise over 30 minutes. The mixture was vigorously stirred for 30 minutes at −50° C. and then quenched with saturated aqueous ammonium chloride. The organic phase was collected and the aqueous phase was extracted with diethyl ether. The organic phases were combined and washed with hydrogen chloride (1M), sodium hydrogen carbonate (sat.), dried, filtered, concentrated and separated by column chromatography (toluene: ethyl acetate, 1:5), to give the title compound (1 g, 64%), [α]$^{22}$D:+1.56° (c 1.03, CHCl$_3$); $^1$H-NMR (100 MHz, CDCl$_3$): 1.8 (m 1H, H-3); 2.13 (t, J$_{1',2'}$=J$_{1',3'}$=6.8 Hz, 2H, H-1'); 3.3 and 3.0 (broad, 2H, OH-2); 3.59 (m, 4H, H-1, H-4); 4.0 (m, 1H, H-2); 4.48 (s, 2H, CH$_2$Ph); 4.94 and 5.09 (m, 2H, H-3'a, H-3'b); 5.78 (m, 1H, H-2'); 7.14–7.5 (m, 4H, arom); $^{13}$C-NMR (25.05 MHz, CDCl$_3$); 30.6 (C-1'); 42.3 (C-3); 63.3 (C-4); 71.9, 72.3, 72.5 (CH$_2$Ph, C-1, C-2'); 116.4 (C-3'); 121.5, 129.1, 131.3 (aromatic C); 136.4 (C-2 and aromatic C);

b) (2S,3R)-4-O-Benzoyl-1-O-p-bromobenzyl-3-C-(2'-propenyl)-1,2,4-butan-triol. Benzoyl chloride (3.21 ml, 27.6 mmol) was added dropwise to a solution of compound 2 (8.54 g, 27 mmol) in dry pyridine (50 ml) at 0° C. The reaction mixture was stirred at 0° C. for 15 minutes. Water (5 ml) was added and the solvent was evaporated. The residue was dissolved in dichloromethane and washed with hydrochloric acid (1M), aqueous sodium hydrogen carbonate (sat.), dried, concentrated and purified by flash chromatography (toluene:ethyl acetate, 2:1) to give the title compound (9.77 g, 86%). $[\alpha]^{22}D:8.5°$ (c 0.71, CHCl$_3$); $^1$H-NMR (100 MHz, CDCl$_3$):1.95–2.43 (m, 3H, H-3, H-1′); 2.59 (d, $J_{H(OH),2}$=3.9 Hz, 1H, OH-2); 3.54 (m, sec. order, 2H, H-1a, H-1b); 3.95 (m, 1H, H-2); 4.34 (d, $J_{4,3}$=5.11 Hz, 2H, H-4); 4.48 (s, 2H, CH$_2$Ph); 5.14 and 5.0 (m, 2H, H-3′a, H-3′b); 5.78 (m, 1H, H-2′); 8.1–7.14 (m, 9H, arom.); $^{13}$C-NMR (25.05 MHz, CDCl$_3$); 31.3 (C-1′; 40.4 (C-3); 70.1 C-2; 64.0 (C-4); 72.3 (CH$_2$/ Ph); 72.5 (C-1); 116.3 (C-3′); 121.4–134.7 (arom.); 136.4 (C-2′); 166.1 (COPh).

c) Methyl 3-C-[(benzoyloxy)methyl]-5-O-p-bromobenzyl-2,3-dideoxy-D-erythro-pentofuranoside. To an ice cold mixture of compound b (7.5 g, 17.9 mmol) and N-methylmorpholine-N-oxide (4.8 g, 35.5 mmol) in tetrahydrofuran:water (3:1, 70 ml), OsO$_4$ in t-Butanol (18 ml, 0.02M, stab. with 1% TBHP, 0.36 mmol) was added. After a few minutes, the ice bath was removed and the reaction mixture was stirred overnight at room temperature under nitrogen. NaHSO$_3$ (2 g) was added and the mixture was stirred for 15 minutes. The solvent was evaporated off and the residue diluted with ethyl acetate, washed with HCl (1M), NaHCO$_3$ (sat.), dried, filtered and concentrated. The crude product was dissolved in tetrahydrofuran:water (3:1, 200 ml) and treated with NaIO$_4$ (7.65 g, 35.8 mmol). The cis diol was completely cleaved after 30 minutes at room temperature. The tetrahydrofuran was evaporated off and the aqueous residue was saturated with NaCl, and extracted with diethyl ether. The organic phase was dried and concentrated. The residue was treated with methanolic HCl (0.05%, 50 ml) for ten minutes, neutralized with Dowex 2×8 (HCO$_3$), filtered, evaporated and the residue was purified by flash chromatography (toluene ethyal acetate, 3:1) to give an anomeric mixture of the title compound (6.63 g, 85%) as a colourless syrup. $^1$H-NMR (100 MHz, CDCl$_3$): 1.7–2.9 (three m, 3H, H-3, H-2a, H-2b); 3.31, 3.35 (2s, 3H, OCH$_3$); 3.6 (m, 2H, H-5); 4.1 (m, 1H, H-4); 4.4 (m, 2H, H-6); 4.6 (m, 2H, CH$_2$Ph); 5.1 (m, 1H, H-1); 7.1–8.0 (m, 9H, aromatic); $^{13}$C-NMR (25.05 MHz, CDCl$_3$): 35.6, 36.4 (C-2); 38.7, 39.3 (C-3); 54.3, 54.5 (OCH$_3$); 65.7, 66.6, (C-6); 71.5, 72.35, 72.37, 73.8 (C-5, CH$_2$Ph); 79.9, 80.1 (C-4); 104.8 (C-1); 121.0–136.4 (aromatic); 165.8 (COPh).

d) Methyl 5-O-benzoyl-3-C-[(benzoyloxy)methyl]-2,3-dideoxy-D-erythro-pentafuranoside. A solution of compound c (1 g, 2,3 mmol) in dry diethyl ether (3 ml) was dissolved in liquid ammonia (50 ml) in a dewar bottle. Sodium (300 mg, 13 mmol) was added in portions over 5 minutes. The solution was stirred for 30 minutes and then quenched with solid NH$_4$Cl. The ammonia was evaporated under a stream of nitrogen and the solid residue was diluted with ethyl acetate. The solid was filtered off and washed several times with ethyl acetate. The filtrate was concentrated and then co-evaporated with dry toluene. The crude residue was dissolved in dry pyridine (30 ml). Benzoylchloride (0.8 ml, 6.9 mmol) was added and the solution was stirred for 40 minutes at room temperature after which water (5 ml) was added and the mixture was concentrated to dryness. The residue was dissolved in CH$_2$Cl$_2$ and washed with aqueous HCl (1M), aqueous NaHC)$_3$ (sat.), dried, filtered and evaporated to dryness. Flash chromatography (toluene ethyal acetate, 3:1) fielded the title compound (580 mg, 68%), as an anomeric mixture. A small sample of the compound was separated by silica gel. $^1$H-NMR and m.p. of the β-anomer were in agreement with those previously reported.

PREPARATION OF INTERMEDIATE PRODUCTS

The starting materials for compounds 11, 17, 14 and 20 in Examples 7, 8, 9 and 10 respectively, were prepared in the following manner:

The carbocyclic ring was built using the sodium cyamide dimerization of diethylmaleate described by Dolly et al. [1].

Cyclopentanone-3,4-dicarboxylique acid-dimethyl ester (compound 1) was dissolved in ethyleneglycol [2]. The solution was saturated with HCl. Ketalization was let to proceed overnight at room temperature. The hydrochloric acid is then removed under 12 mmHg pressure, at room temperature. Distillation under reduced pressure (<1 mmHg) allows 1-dioxolano-3,4-dicarboxylic acid dimethyl ester to be isolated.

The above product is a 1:1 mixture of Cis and trans dicarboxylic acids dimethyl esters (compound 2), which can be isomerized mainly (30%) to the trans form under the following conditions. The ketal is dissolved in toluene-methanol (5:1, 10 ml/g) and sodium methylate (0.3 eq) is added and the whole is warmed at 50° C. for five hours. The reaction is then poured into water and extracted with ethylacetate to give compound 3.

$^{13}$C-NMR (CDCl$_3$): 173.5 (2) ester carbonyl; 114.9 (s) C-1; 64.0 (t, $J_{CH}$=147.74 H3) dioxolano; 51.6 (q, $J_{CH}$=147.74 H3) OCH$_3$; 43.5 (d, $J_{CH}$=173.3 H3) C-3 and C-4; 38.6 (t, $J_{CH}$=133.0 H3) C-2 and C-5.

1. L. J. Dolly, S. Esfandiari, C. A. Elligor, K. S. Marshall. J. Eng. Chem., 36, 1277 (1971).
2. B. G. Howard, R. V. Lindsey. J. Am. Chem. Soc., 82, 158 (1960)

1-Dioxolano-3,4-trans-dicarboxylic acid dimethyl ester (compound 3) is suspended in tetrahydrofuran (10 ml/g) and lithium aluminium hydride (0.32 g/g starting material) is added portionwise, with a fast stirring, sufficiently quickly to keep a mild reflux. Stirring is pursued for 1 hour after the addition is complete. The reaction is then poured into ethylacetate and filtered over a Celite bed. After evaporation of the solvent, the crude material is used in the next step.

1-Dioxolano-3,4-trans-C-dihydroxymethyl (compound 4) (7,8 g, 44.6 mmol) is dissolved into THF–DMF mixture (9:1) and added to a suspension of 80% sodium hydride (2.81 g, 94 mmol) in the same solvent, under reflux. Some 30 minutes later, neat benzyl bromide is added dropwise under reflux. Reflux is pursued for 2 hours after addition is complete. After cooling, the reaction is poured into ethylacetate and thoroughly washed with water.

The crude dibenzylated material (compound 5) is then dissolved in dichloromethane, containing 15% isopropanol (5 ml/mmol) and toluene sulfonic acid monohydrate (1.05 eq) is added. Stirring is pursued for 4 hours, after which the reaction is poured into 0.01N NaOH and extracted with dichloromethane. Purification by column chromatography, using hexane-ethylacetate 1:1 as the eluent gives 1-oxo-3,4-trans-di-C-hydroxymethyl-3,4-di-O-benzyl-cyclopentane (compound 6) (27.6 mmol, 9 g) in 62% overall yield.

$^1$H-NMR (CDCl3): S 7.30 (m, 10H) benzyl aromatic fractions; 4.5 (2, 4H) benzyl CH$_2$; 3.5 (m, 4H) CH$_2$O; 2.5 (m, 4H) H-2 and H-5; 2.2 ( m, 2H) H-3 and H-4.

$^{13}$C-NMR (CDCl$_3$): 138.3, C-1; 127.9 and 126.8 benzyl aromatic carbons; 73.0, benzyl CH$_2$; 72.2, —CH$_2$O—; 41.7, C-3 and C-4; 38.9, C-2 and C-5.

A solution of compound 6 (0.50 g, 1.54 mmol) in EtOH (30 ml) was heard to reflux and K$_2$CO$_3$ (0.300 g, 2.2 mmol) was added followed by NH$_2$OH×HCl (0.26 g, 3.71 mmol) in small portions. The solution was cooled and diluted with H$_2$O (100 ml) and extracted with CH$_2$Cl$_2$ (3×50 ml). The combined extracts were dried with Na$_2$SO$_4$ and evaporated. The residue was dissolved in THF (50 ml) and LAH (0.23 g, 6.16 mmol) was carefully added. The solution was refluxed for 5 hours cooled and quenched with H$_2$O (1 ml). The solution was diluted with Et$_2$O (200 ml) and filtered through celite.

The solution was washed with H$_2$O (3×20 ml), extracted with HCl (aq) (3×20 ml), extracted with HCl (aq) (3×20 ml 2M) and the aqeous phase was made alcaline with NaOH (aq) to pH 14.

The aqeous phase was extracted with Et$_2$O (3×20 ml), the combined extracts were dried with NaSO$_4$ and evaporated to give a pale yellow oil. The oil was purified by flash chromatography on silica gel (Merck Si 60) by elution with CH$_2$Cl$_2$/MeOH/NH$_3$ 95:3:2. The pure fractions were evaporated to give 1-[(3,4-trans-C-dibensyloxymethyl)cyclopentyl]amine (compound 8) as an oil.

$^1$H-NMR Bruker 250 MHz, (CDCl$_3$, 1.3–2.5 ppm—CHCH$_2$O, 2H, CH$_2$ CHNH$_2$ 4H, 3.3–3.7 CH$_2$O, 4H, 4.4–4.7 Ph—CH$_2$, 4H, CHNH$_2$, 1H, NH$_2$2H, 7.3–7.4 ppm C$_6$H$_5$/ —CH$_2$ 10H.

BIOLOGICAL TESTS

Tests I Effects of compounds of the formula I on HIV in H9 cells

TABLE 1

Inhibition of human immunodeficiency virus multiplication in cell culture

| Compounds | Concentration | Inhibition % |
|---|---|---|
| | μM | |
| 1-(3-fluoro-2,3,-dideoxy-α-D-ribofuranosyl)-5-ethyluracil (VSA 411)* | 0.1 | 50 |
| 1-(3-fluoro-2,3,-dideoxy-α-D-ribofuranosyl)-5-propyluracil (VSA 409)* | 2.5 | 50 |
| 1-(2-deoxy-α-D-ribofuranosyl)-5 ethyluracil (VIP 289)* | 10 | 50 |
| 1-[2',3'-Dideoxy-3'C-(hydroxymethyl)-a-D-erythro-pentafuranosyl] cytosine (compound 21)* | 5 | 50 |
| 1-[2',3'-Dideoxy-3'C-(hydroxymethyl)-a-D-erythro-pentafuranosyl] thymine (compound 22)* | 10 | 50 |
| | μg/ml | |
| 1-[(3,4-trans-C-dihydroxymethyl)cyclopentyl] uracil (compound 11)** | 10 | 23 |
| 1-[(3,4-trans-C-dihydroxymethyl)cyclopentyl] thymine (compound 17)** | 10 | 33 |
| 1-[(3,4-trans-C-dihydroxymethyl)cyclopentyl] pentyl] cytosine (compound 14)** | 10 | 39 |

TABLE 1-continued

Inhibition of human immunodeficiency virus multiplication in cell culture

| Compounds | Concentration | Inhibition % |
|---|---|---|

*The tests were performed as described in the specification of the application: H9 cells, 10$^5$ cells per well on a 24-well plate, suspended in 2 ml RPMI-medium containing 10% fetal calf serum, 100 ug/ml penicillin, 10 ug/ml streptomycin sulfate and 2 ug/ml polybrene are exposed to HIV (HTLV-IIIB) and different concentrations of the test compounds. The plates are incubated at 37° C. in 5% CO$_2$ for 6–7 days. The contents in each well is then homogeneized with a pipette and transferred to a centrifuge tube. After centrifugation for 10 min at 1500 rpm the supernatant is removed and the cell pellet is analyzed by fixing in methanol on glass plates. Human HIV positive serum diluted 1:80 or 1:160 is added and incubated for 30 min at 37° C. The plate is then washed with phosphate-buffered saline (PBS) containing Ca$_2$+ and Mg$_2$+. Sheep antihuman conjugate (FITC) is added and after a new incubation the plate is again washed with PBS. Contrast staining is done with Evans blue and after drying the frequency of HIV antigen containing cells is determined in a microscope.

**HIV-RT was assayed in 96-well microtiter plates using 10$^4$ H9 cells per cell. The compounds to be tested were added in different concentrations before infection with cell-free HIV-1. The infecting dose of HIV-1 was adjusted to give a RT activity of 15.000–40.000 cpm in 15 μM culture supernatant at harvest after 6 days of incubation. RT activity was determined in 15 μl culture supernatant treated with virus disruption buffert, VDB (100 mM Tris HCl pH = 7.6, 100 mM KCl, 4 mM DTT, 1 mM EDTA and 1.25% Triton X-100) in a final volume of 50 ul containing 100 mM Tris HCl pH 7.6, 100 mM KCl, 4 mM MgCl2, 4 mM DTT, 0.25 μg (rA)n (dt)12–18 (Pharmacia, Uppsala, Sweden) 14 ug bovin serum albumin (fraction V) and 0.6 μM $^3$H-dTTP (specific activity 18.700 cpm/pmol; New England Nuclear Corp; Boston, MA). The reaction product was collected on a filter sheet prewetted and washed with 10% TCA-0.02 M sodium pyrophosphate using Titertek cell harvester. 96 filter discs were plunged out from each filter sheet and the radioactivity counted in scintillation fluid. The anti-HIV activity is given as % reduction of RT activity measured in the infected controls (at least four per microtiter plate).

It is seen in Table 1 that the tested copounds are active inhibitors of HIV virus multiplication.

Test II Cellular toxicity

TABLE 2

Cellular toxicity on H9 and F5000 cells.

| Compound | H9 | F5000 |
|---|---|---|
| | TC$_{50}$ (μM) | |
| 1-(3-fluoro-2,3,-dideoxy-α-D-ribofuranosyl)-5-ethyluracil (VSA 411) | 400 | 500 |
| 1-(3-fluoro-2,3,-dideoxy-α-D-ribofuranosyl)-5-methyluracil (VSA 419) | | 250 |
| 1-(2-deoxy-α-ribofuranosyl)-5-ethyluracil (VIP 289) | | 1000 |
| | TC$_{50}$ (μg/ml) | |
| 1-[(3,4-trans-C-dihydroxymethyl)-cyclopentyl] uracil (compound 11) | >>100 | |
| 1-[(3,4-trans-C-dihydroxymethyl)-cyclopentyl] thymine (compound 17) | ~100 | |
| 1-[(3,4-trans-C-dihydroxymethyl)-cyclopentyl] cytosine (compound 14) | >>100 | |

H9 cells, 2×10$^7$ cells per plate, are incubated in RPMI-1640 medium containing 10% fetal calf seizure, 70 mg/l penicillin, 100 mg/l streptomycin and 10 mM hepes, in absence or presence of test compounds. The number of cells per plate is determined after 48 hrs. Cells incubated in absence of test compound then underwent two cell division cycles.

F5000 cells, which are human embryo cells, 1×10$^5$ cells per plate, are incubated in Eagle's minimal essential medium, supplemented with Earle's salts, non-essential amino acids, 10% fetal calf serum, 10 mM hepes, 70 mg/l penicillin and 100 mg/l streptomycin, in absence or presence of test compounds. The number of cells per plate is determined after 48 hrs. Cells incubated in absence of test compounds underwent one cell division cycle. The results are given as TC$_{50}$, which is the concentration of a compound which gives 50% inhibition of cell multiplication.

It is seen in Table 2 that the test compounds exhibit TC$_{50}$ values which vastly exceed the concentration needed for inhibition of HIV virus multiplication according to Table 1.

We claim:

1. A method of treating Hepatitis B virus infections which comprises administering to a patient in need of such treatment an effective anti-hepatitis B amount of a compound of the formula:

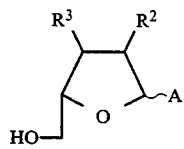

wherein A is

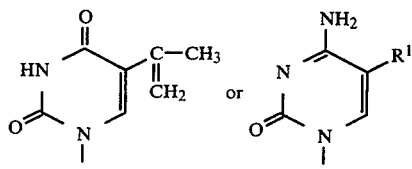

R$^1$ is H or

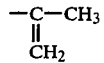

R$_2$ is H; and
R$^3$ is F or CH$_2$OH; with the proviso that when R$^1$ is H, then R$^3$ is not F; or a therapeutically acceptable salt thereof.

* * * * *